(12) United States Patent  
Crawford, Jr. et al.

(10) Patent No.: US 11,213,644 B2  
(45) Date of Patent: Jan. 4, 2022

(54) MULTIPLE CONTROL INTERFACE FOR MEDICAL VENTILATOR

(71) Applicant: Nihon Kohden OrangeMed, Inc., Santa Ana, CA (US)

(72) Inventors: Richard William Crawford, Jr., Yucaipa, CA (US); Hong-Lin Du, Irvine, CA (US); Steven F. Landas, Riverside, CA (US); Phuoc Huu Vo, Anaheim, CA (US)

(73) Assignee: Nihon Kohden OrangeMed, Inc., Santa Ana, CA (US)

( * ) Notice: Subject to any disclaimer, the term of this patent is extended or adjusted under 35 U.S.C. 154(b) by 276 days.

(21) Appl. No.: 16/326,903

(22) PCT Filed: Jul. 25, 2017

(86) PCT No.: PCT/US2017/043781  
§ 371 (c)(1),  
(2) Date: Feb. 20, 2019

(87) PCT Pub. No.: WO2018/038853  
PCT Pub. Date: Mar. 1, 2018

(65) Prior Publication Data  
US 2019/0184119 A1  Jun. 20, 2019

Related U.S. Application Data

(60) Provisional application No. 62/378,888, filed on Aug. 24, 2016.

(51) Int. Cl.  
*A61M 16/00* (2006.01)  
*G06F 21/00* (2013.01)  
(Continued)

(52) U.S. Cl.  
CPC ......... *A61M 16/024* (2017.08); *A61G 10/005* (2013.01); *A61M 15/00* (2013.01);  
(Continued)

(58) Field of Classification Search  
CPC ........ A61M 16/00; A61M 16/021–024; A61G 10/00–04; G06F 21/00; G06F 21/30–31;  
(Continued)

(56) References Cited

U.S. PATENT DOCUMENTS 6,369,838 B1  4/2002  Wallace et al.  
7,188,621 B2  3/2007  DeVries et al.  
(Continued)

FOREIGN PATENT DOCUMENTS

AU  749840 B2  7/2002  
CN  101821743 A  9/2010  
(Continued)

OTHER PUBLICATIONS

Extended European Search Report for Application No. 17844092.1, dated Mar. 25, 2020.  
(Continued)

*Primary Examiner* — Thaddeus B Cox  
(74) *Attorney, Agent, or Firm* — Dorsey & Whitney LLP (57) ABSTRACT

Examples described herein include multiple control systems for medical devices, such as medical ventilators. Examples of multiple control of a medical ventilator in an isolation room are described.

18 Claims, 7 Drawing Sheets

(51) Int. Cl.
*G06F 21/44* (2013.01)
*G06F 21/60* (2013.01)
*G16H 40/67* (2018.01)
*H04L 29/08* (2006.01)
*A61M 15/00* (2006.01)
*A61G 10/00* (2006.01)
*A61B 5/08* (2006.01)
*A61B 5/00* (2006.01)

(52) U.S. Cl.
CPC ........ *A61M 16/00* (2013.01); *A61M 16/0051* (2013.01); *G06F 21/00* (2013.01); *G06F 21/44* (2013.01); *G06F 21/606* (2013.01); *G16H 40/67* (2018.01); *H04L 67/12* (2013.01); *A61B 5/0816* (2013.01); *A61B 5/4836* (2013.01); *A61M 2205/3561* (2013.01); *A61M 2205/3592* (2013.01); *A61M 2205/502* (2013.01); *A61M 2205/52* (2013.01); *A61M 2205/581* (2013.01); *A61M 2205/583* (2013.01); *A61M 2230/63* (2013.01)

(58) Field of Classification Search
CPC ....... G06F 21/34–35; G06F 21/44–445; G06F 21/60; G06F 21/606; G16H 40/67
See application file for complete search history.

(56) References Cited

U.S. PATENT DOCUMENTS

| | | |
|---|---|---|
| 2002/0099477 A1 | 7/2002 | Wallace et al. |
| 2005/0051168 A1 | 3/2005 | Devries et al. |
| 2007/0180129 A1* | 8/2007 | Tolmie .................. H04W 4/029 709/230 |
| 2012/0000470 A1 | 1/2012 | Milne et al. |
| 2012/0123219 A1* | 5/2012 | Georgiev ................. A61B 5/08 600/300 |
| 2013/0199533 A1 | 8/2013 | Steinhauer et al. |
| 2013/0204145 A1 | 8/2013 | Shah |
| 2014/0000609 A1* | 1/2014 | Steinhauer ........ A61M 16/0051 128/204.23 |
| 2015/0120067 A1 | 4/2015 | Wing et al. |
| 2016/0301691 A1* | 10/2016 | Miller ....................... G01S 5/14 |
| 2017/0000412 A1* | 1/2017 | Scott ...................... G16H 20/40 |
| 2019/0286844 A1* | 9/2019 | Gross ..................... H04L 67/18 |

FOREIGN PATENT DOCUMENTS

| | | |
|---|---|---|
| CN | 102047256 A | 5/2011 |
| CN | 102186524 A | 9/2011 |
| MX | 2014013952 A | 3/2015 |
| WO | 2014005106 A1 | 1/2014 |
| WO | 2015020536 A1 | 2/2015 |
| WO | 2015161345 A1 | 10/2015 |

OTHER PUBLICATIONS

International Search Report and Written Opinion for PCT App No. PCT/US2017/043781, dated Sep. 27, 2017.

English translation of Notice of Reasons for Refusal received in JP App. No. JP 2019-531854 dated May 25, 2021.

English summary of First Office Action received in CN App. No. 201780052114.2 dated May 14, 2021.

\* cited by examiner

MULTIPLE CONTROL INTERFACE FOR MEDICAL VENTILATOR

TECHNICAL FIELD

Examples described herein relate generally to a breathing apparatus, such as a medical ventilator, and to the control of the breathing apparatus. Examples of control of medical ventilators for the isolation rooms are described.

BACKGROUND

A breathing apparatus such as a medical ventilator is generally connected to a patient through a breathing circuit, such as a breathing tube. The medical ventilator delivers gases to the patient from a gas delivery unit and permits the patient to exhale by controlling a delivery flow with or without an exhalation valve. A medical ventilator is usually provided with an interface that allows a user (e.g., medical practitioners, health care workers) to change settings of the medical ventilator as well as to view monitored parameters and alarm statuses. The interface for controlling the medical ventilator is usually located at a bedside of the patient.

Problems arise sometimes when there is only one interface for controlling the medical ventilator. One example is when only one interface is provided with the medical ventilator inside the isolation room for a patient with contagious diseases. Another example is when the patient needs stay inside a clean isolation room. Since the medical practitioners and/or the health care workers are not attending in the isolation room at all hours, entering the isolation room may require a person to spend time to wear personal protective equipment (PPE) (e.g., a cap, a gown, a mask, and a pair of gloves, etc.) to protect the person from being infected or to prevent spreading biohazard in the isolation room. When a condition of the patient suddenly deteriorates, the medical practitioners and/or the health care workers may need to operate the medical ventilator urgently to change settings of the medical ventilator or to perform an urgent maneuver such as manual ventilation. However, donning the PPE may take ten to fifteen minutes before entering the isolation room which may delay the action to provide urgent care including time-critical ventilator management to the patient who is treated under mechanical ventilation. Another example of the problem with the only one interface is when the patient needs to be put on certain maneuver (e.g., inspiratory hold) in order to get a stable chest image in a computed tomography (CT) examination where the medical practitioners and/or the health care workers may be away from the patient bedside to prevent from radiologic hazard exposure. In these situations, there is clearly a need of interface(s) in addition to the primary interface that is closely at the patient bedside.

SUMMARY

Examples described herein include multiple control systems and methods for medical devices, such as medical ventilators. Examples of multiple control of a medical ventilator in an isolation room are described. An example multiple control system includes: a first interface inside a first area, a second interface inside a second area that is medically isolated from the first area, a ventilator, a controller, a first communication path and a second communication path. The first interface includes: a first monitor that presents data related to control of a ventilator; a first input device that receives a first command; and a first communication device that provides the data to the first monitor, and further receives the first command from the first input device and to communicate the first command. The second interface is configured to be coupled to the ventilator. The second interface includes: a second monitor that presents the data; a second input device that receives a second command; and a second communication device that provides the data to the second monitor, and receives the second command and to communicate the second command. The ventilator is inside the second area and provides treatment to a patient. The controller is inside the second area and receives the first command from the first communication device and the second command from the second communication device and further controls the ventilator responsive to a command received. The first communication path is coupled to the first communication device and further coupled to the controller. The first communication path traverses between the first area and the second, medically isolated, area and carries the first command to the controller. The second communication path in the second area, coupled to the second communication device and further coupled to the controller, and carries the second command to the controller.

Another example medical ventilation system includes a first interface inside a first area, a second interface, a ventilator and a controller inside a second area, a first communication path coupled to the first communication device and further coupled to the controller, and a second communication path in the second area. The first interface includes a first monitor that presents data related to control of a ventilator; a first input device that receives a first command; and a first communication device that provides the data to the first monitor, and further receives the first command from the first input device and to communicate the first command. The second interface is coupled to the controller and further coupled to the ventilator. The second interface includes a second monitor that presents the data; a second input device that receives a second command; and a second communication device that provides the data to the second monitor, and further receives the second command and to communicate the second command. The ventilator is coupled to a body of a patient. The controller receives the first command from the first communication device and the second command from the second communication device and further controls the ventilator responsive to a command received. The first communication path traverses between the first area and the second area and carries the first command to the controller. The second communication path is coupled to the second communication device and further coupled to the controller, and carries the second command to the controller. The controller verifies a state that the first interface is within a visible range from the controller responsive to the first command, and further configured to reject the first command if the controller fails to verify the state.

An example multiple control method of controlling a ventilator includes steps of: clinically isolating a first area from a second area; electrically coupling a first interface in the first area to a controller in the second area; electrically coupling a second interface in the second area to a controller in the second area; transmitting first control information to the controller from the first interface of the first area; transmitting second control information to the controller from the second interface of the first area; receiving the first control information from the first interface and the second control information from the second interface by the controller in the ventilator in the second area; and controlling the ventilator in the second area to provide treatment to a patient in the second area by the controller responsive to the first control information.

DETAILED DESCRIPTION OF PREFERRED EMBODIMENTS

Examples of medical ventilator systems that may include an interface outside of a room in which the medical ventilator and patient are located, in addition to an interface inside the room, used to control a medical ventilator inside the room, are described herein. While operating the medical ventilator, a patient within an isolation or other room may be directly viewed by a user who operates the ventilator outside of the room for patient safety or for patient diagnosis purposes while the person may be protected from biohazard or radiologic hazard in the room. By operating the interface outside the room and within sight of the user, the user may provide timely treatment using the medical ventilator to the patient without entering the room. Thus, potential exposure to biologic/radiologic hazard by entering the room may be minimized, and sufficient time to don PPE prior to entering the room may be secured.

Various embodiments of the present invention will be explained below in detail with reference to the accompanying drawings. The following detailed description refers to the accompanying drawings that show, by way of illustration, specific aspects and embodiments in which the present invention may be practiced. These embodiments are described in sufficient detail to enable those skilled in the art to practice the present invention. Other embodiments may be utilized, and structure, logical and electrical changes may be made without departing from the scope of the present invention. The various embodiments disclosed herein are not necessary mutually exclusive, as some disclosed embodiments can be combined with one or more other disclosed embodiments to form new embodiments.

Figure 1:
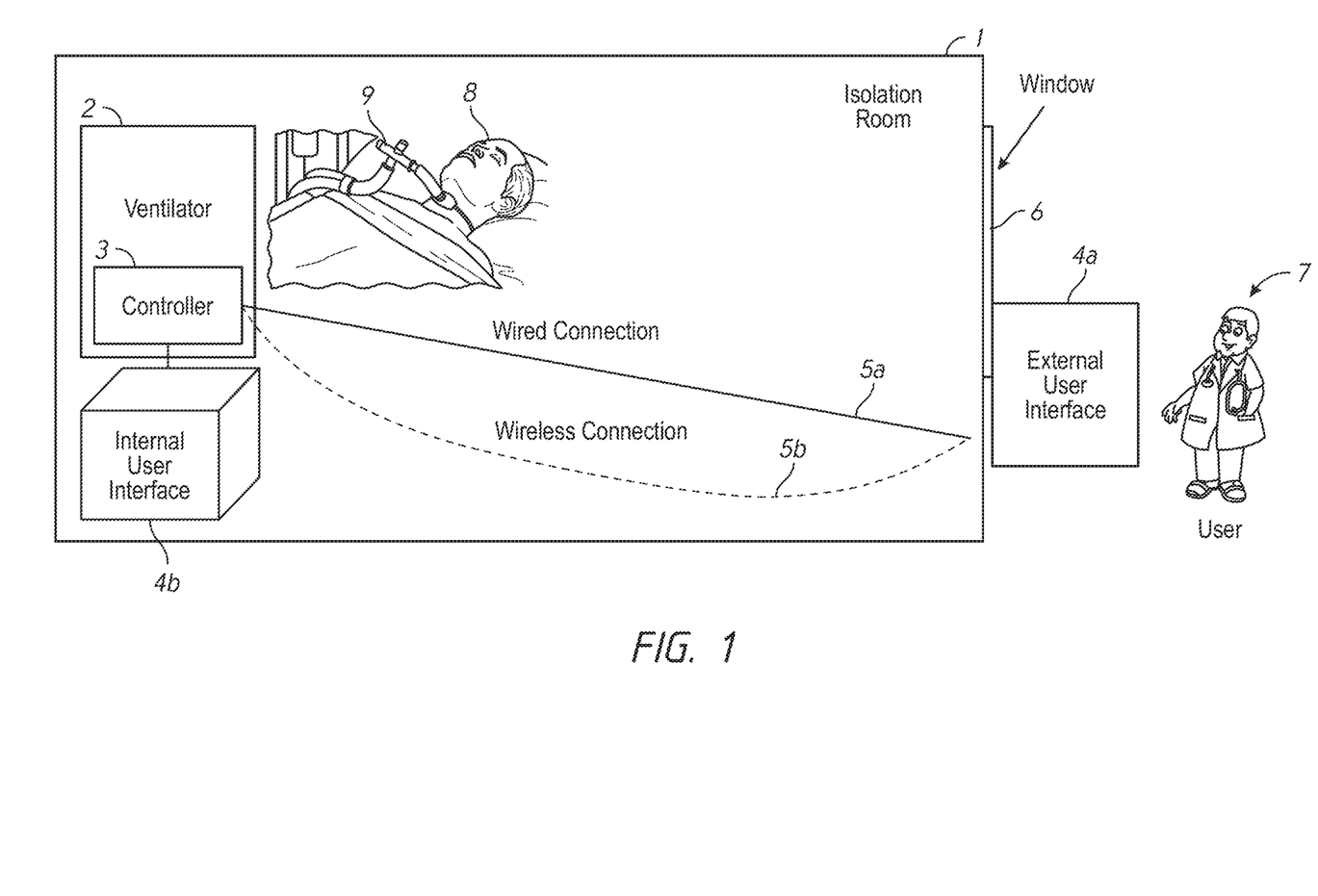
FIG. 1 is a schematic diagram of a medical ventilation system including a medical ventilator and interfaces according to an embodiment of the present disclosure.

Examples of breathing apparatuses such as a medical ventilator and the control of the medical ventilator are described herein. While ventilators are described by way of example, in other examples, other medical devices may be controlled using internal and external control interfaces described herein which allow for control of the medical device from outside an isolation room while still viewing the patient inside the isolation room. Examples of other medical devices include, but are not limited to infusion pumps. The alternate interface to the medical device (e.g. medical ventilator) may provide capability to control the medical device (e.g. change settings, alter operation of the medical device) and provide a display of status of the medical device at a near-range location. FIG. 1 is a schematic diagram of a medical ventilation system including a medical ventilator and interfaces according to an embodiment of the present disclosure. For example, a medical ventilation system may include a second user interface 4a in a first area which may be outside of a second area medically isolated from the first area, such as an isolated room 1. For example, the isolation room 1 may be an intensive care unit (ICU) used to prevent or reduce infections by sealing contents therein. The isolation room 1 may be a computed tomography (CT) scanner or any radiographic imaging room used to prevent or reduce radiation exposure. The medical ventilation system may include a ventilator 2 inside the isolation room 1. For example, the ventilator 2 may be a mechanical ventilator that provides treatment, such as gas including oxygen, through a tube 9 to a patient 8 inside an isolation room 1. The patient 8 may be located in a visible range to a user 7. The user may be a medical practitioner or a qualified healthcare worker who operates the external user interface 4a. The isolation room 1 may include a window 6. The window 6 may be made of transparent or at least partially transparent material, such as glass, plastic, carbon, etc., which may be a visual path to provide a view of the patient 8 while isolating the inside the isolation room 1 from the outside the isolation room 1 to prevent or reduce hazardous radiation, contamination and infections of the user outside the isolation room 1. The medical ventilation system may further include a controller 3 in the ventilator 2 inside the isolation room 1. When the user 7 in the first area operates the external user interface 4a and enters an external command, the controller 3 may receive the external command from the external user interface 4a and may further control the ventilator 2 responsive to the external command. The medical ventilation system may further include a communication path that traverses between the first area and the second, medically isolated, area. The communication path may couple the external user interface 4a and the controller 3. The communication path may be a wired connection 5a or a wireless connection 5b. For example, the wired connection 5a may be implemented using twisted pairs of cables made of conductive material (e.g., copper, etc.), coaxial cables, fiber optic cables made of light-conductive material (e.g., glass, silicon, plastic, etc.). For example, the wireless connection 5b may be implemented using infrared, microwaves, radiowaves, Wi-Fi, Bluetooth, etc. The communication path may carry the external command from the external user interface 4a to the controller 3. The medical ventilation system may further include an internal user interface 4b inside the isolation room 1 coupled to the controller 3. The controller 3 inside the isolation room 1 may also receive an internal command from the internal user interface 4b and may further control the ventilator 2 responsive to the internal command.

Figure 2:
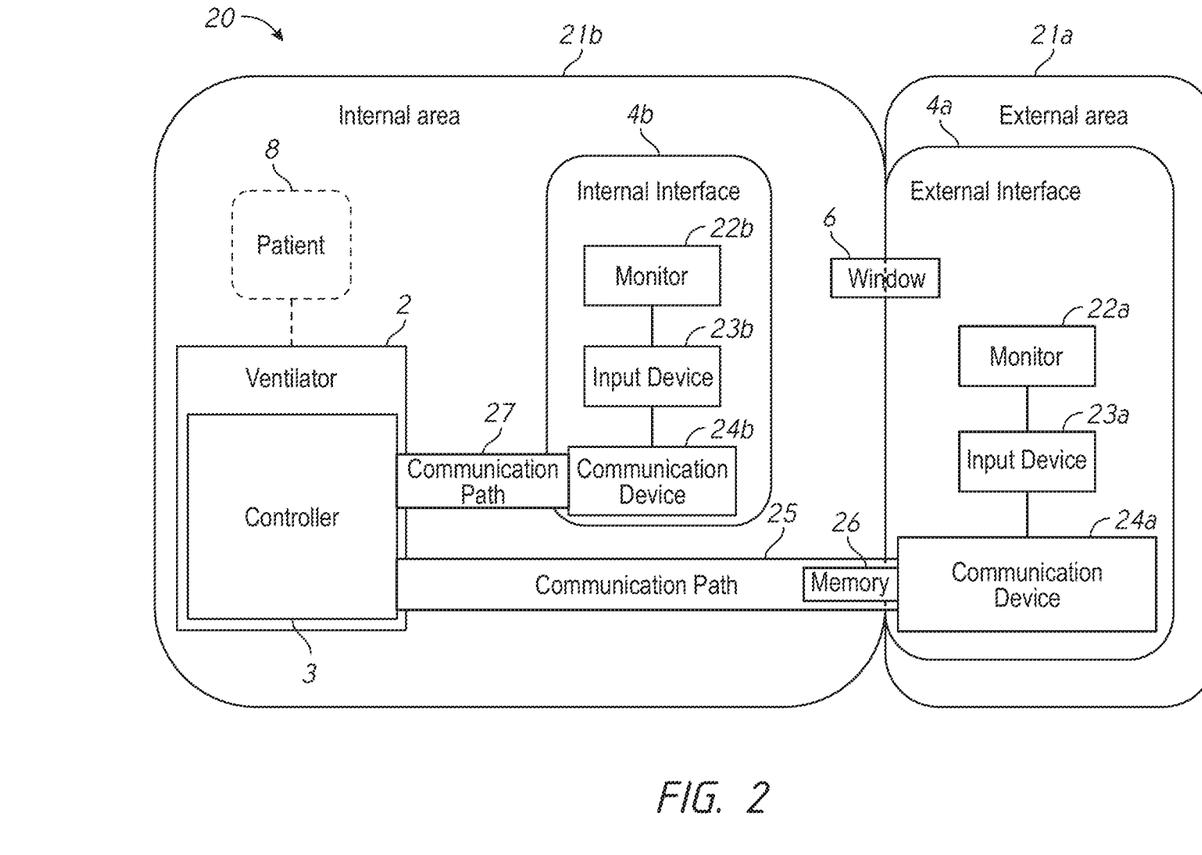
FIG. 2 is a simplified block diagram of a medical ventilation system including a wired connection according to an embodiment of the present disclosure.

FIG. 2 is a simplified block diagram of a medical ventilation system 20 including a wired connection according to an embodiment of the present disclosure. Description of components corresponding to components included in FIG. 1 will not be repeated, and changes from FIGS. 4A and 4B, including configuration of a plurality pairs of inductors will be described. The medical ventilation system 20 may include an external area 21a and an internal area 21b that may be medically isolated from the external area 21a. For example, the external area 21a may be outside the isolation room 1. The external area 21a may include an external interface 4a. The external interface 4a may include a monitor 22a which presents data related to control of the ventilator 2 inside the external area 21a. For example, the data may be patient respiratory frequency, volume, pressure, mechanics and so on. The external interface 4a may include an input device 23a that receives a command from a user, such as the user 7. Any of a variety of commands may be provided to control (e.g. alter the operation of) the ventilator. Examples of commands including, but are not limited to, change pressure, change volume, change flow, start, pause, and/or stop ventilation). The external interface 4a may further include a communication device 24a which may provide the data to the monitor 22a. The communication device 24a may receive the command from the first input device 23a and communicate the command. For example, the internal area 21b may be inside the isolation room 1. The internal area 21b may include a ventilator 2 coupled to a patient 8 in proximity to the ventilator 2, a controller 3 in the ventilator 2 and a communication path 25 coupled to the communication device 24a in the external area 21a and further coupled to the controller 3. The communication path 25 may traverse between the external area and the internal, medically isolated, area. The communication path 25 may carry the command from the first input device 23a to the controller 3. For example, the communication path 25 may be a wired communication via a cable that may have a length shorter than a predetermined length, to ensure the proximity. For example, the cable may be designed to have a length to limit a distance between the user 7 in the external area 21a and the patient 8 in the internal area to about 40 feet in some examples, 50 feet in some examples, 30 feet in some examples. In other examples, other distances may be used. When the user 7 in the external area 21a enters a command from the input device 23a, the communication device 24a may communicate the command and the command may be carried through the communication path to the controller 3. Thus, the controller 3 may receive the command from the communication device 24a via the communication path 25 and may further control ventilation functions of the ventilator 2 responsive to the command.

In one embodiment, the medical ventilation system 20 may further include an internal interface 4b inside the internal area 21b, which may be coupled to the controller 3 in the ventilator 2 via a communication path 27. For example, the internal interface 4b may be installed on a ventilator chassis that houses the ventilator 2. The internal interface 4b may include a monitor 22b that may present the data to a user (not shown) inside the internal area 21b. The internal interface 4b may include an input device 23b that receives a command from the user inside the internal area 21b. The internal interface 4b may further include a communication device 24b coupled to the communication path 27. The communication device 24b may provide the data to the monitor 22b. The communication device 24b may further receive the command and communicate the command through the communication path 27. The communication path 27 may carry the command from the second input device 23b to the controller 3. When the user in the internal area 21b enters a command from the input device 23b, the communication device 24b may communicate the command and the command may be carried through the communication path 27 to the controller 3. Thus, the controller 3 may receive the command from the communication device 24b via the communication path 27 and may further control ventilation functions of the ventilator 2 responsive to the command.

For presenting the data to the user(s) in the external area 21a and the internal area 21b, the controller 3 may further provide the data to the first communication device 24a and the second communication device 24b. The monitors 22a and 22b may receive the data from the communication devices 24a and 24b respectively and present the data. For example, the monitor 22a or the monitor 22b may be a display monitor that displays the data, and/or a sound monitor that may announce the data or may provide sound alerts in case of an alarming condition based on the data.

The user in either the external area 21a or the internal area 21b may operate the input device 23a in the external area 21a or the input device 23b in the internal area 21b, respectively to enter a command. Once the controller 3 receives the command from the input device 23a or the input device 23b from the communication device 24a or the communication device 24b via the communication path 25 or the communication path 27, the controller 3 in the ventilator may control ventilation functions of the ventilator 2 responsive to the command. When a user in the external area 21a and another user in the internal area 21b enter commands substantially at the same time, the medical ventilation system 20 may prioritize the commands. In one embodiment, the controller 3 may discard a first command from the external interface 4a in the external area 21a and may further control the ventilator 2 responsive to a second command from the internal area 21b, if the controller 3 receives the second command within a predetermined time from a receipt of the first command. By prioritizing this manner, it is possible to override a first command execution by a second command execution from the internal interface 4b in the internal area 21b, if the second command is received soon enough after the receipt of the first command.

In one embodiment, the controller 3 may verify a state that the external interface 4a is within a visible range from the controller 3, and the controller 3 may reject the first command if the controller 3 fails to verify the state. For example, the controller 3 may receive an identification item and verify the state by verifying if the identification item satisfies a predetermined condition. The controller 3 may further reject the first command if the identification item fails to satisfy the predetermined condition. The identification item may be a cable ID, a user ID on a user ID card for medical practitioners, a combination of a user logon ID and a passcode to log on the system, biometric information of the medical practitioners, etc. For example, the identification item may be a cable ID uniquely assigned which identifies that the cable satisfies predetermined conditions. In one embodiment, the communication path 25 may include a memory 26 which may be implemented using a non-volatile read-only memory, which may store the identification item, such as the cable ID. For example, the communication path 25 may include a cable that is custom made to limit the distance earlier described and may further embed the memory 26 such as an electrically erasable programmable read-only memory (EEPROM) storing an identifier to the cable. When the communication path 25 is coupled to the controller 3 that controls the ventilator 2, the controller 3 may read the identifier in the EEPROM.

In one embodiment, the controller 3 may provide the data associated with an alert to a user via the internal interface 4b and may further provide the data associated with the alert via the external interface 4a, if the identification item fails to satisfy the predetermined condition. For example, the controller 3 may provide an alert signal to the monitor 22b in the internal interface 4b. The monitor 22b in the internal interface 4b may provide a visual alert on a display on the monitor 22b or a sound alert playing an alert sound from a speaker a speaker in the monitor 22b or a speaker in a pneumatics module, etc.) responsive to the alert signal from the controller 3, if the controller 3 fails to verify the communication path 25 based on the identifier. In one embodiment, coupling a cable to a port of the controller 3 without a memory (e.g. an EEPROM) storing a valid identifier may result in a continuous alert indicating that the identifier for the cable is fraudulent. While the alert is being provided, the controller 3 may accept commands from the input device 23b of the internal interface 4b. The controller 3 may reject commands from the external interface 4a. Once the controller 3 verifies that the identifier is valid, the controller 3 may accept commands from the external interface 4a.

Communication between devices (e.g., the monitor 22a, the input device 23a and the communication device 24a in the external interface 4a, the monitor 22b, the input device 23b and the communication device 24b in the internal interface 4b) may use device inter-device communication. For example, the communication between the devices in the external interface 4a may use a serial bus (e.g., Inter-integrated circuit bus) for communicating and setting control information. This serial bus may also provide control of configurations of the monitors 22a and 22b (e.g., backlight brightness, alarm LEDs, alert sound volume, etc.). During normal operations, a watchdog timer may be used to activate appropriate alerts if communication is lost for any reason with the ventilator 2.

Figure 3:
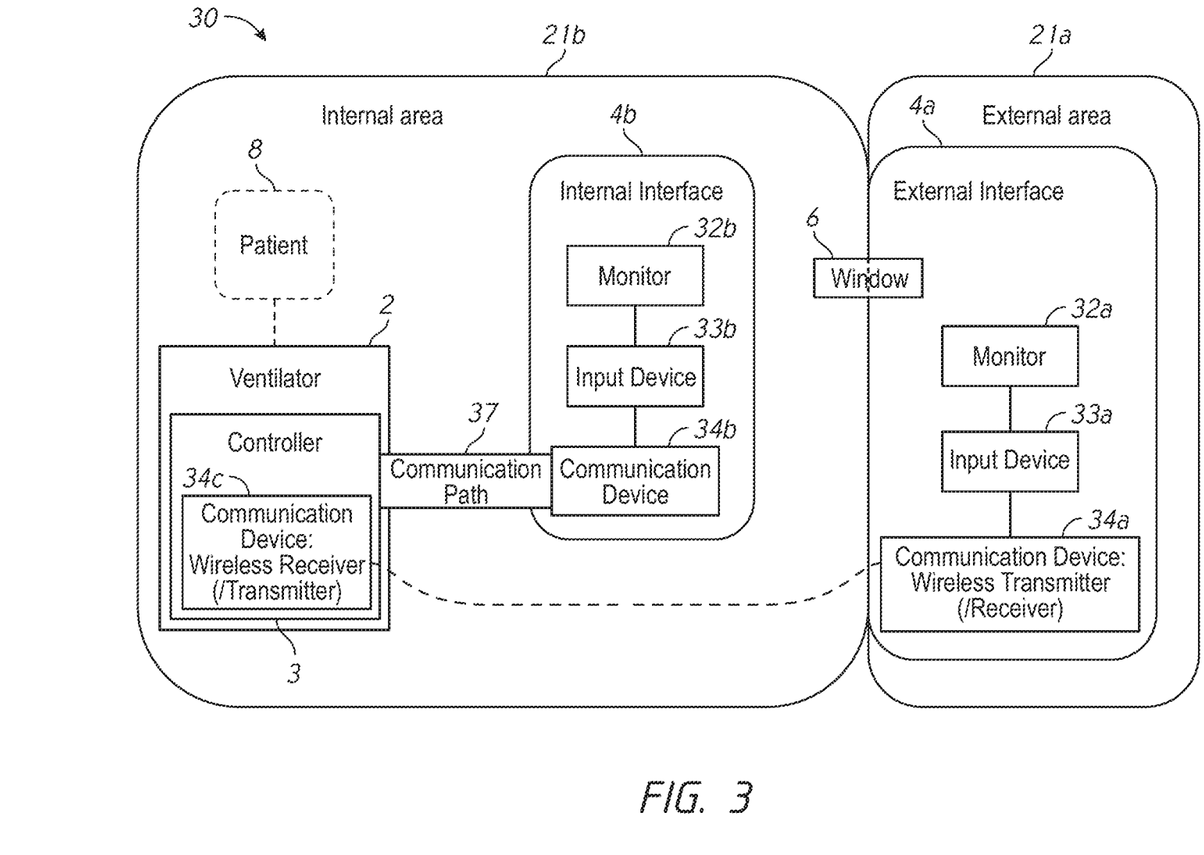
FIG. 3 is a simplified block diagram of a medical ventilation system including a wireless connection according to an embodiment of the present disclosure.

In one embodiment, a communication path may be provided by wireless connection. The communication path may be wired or wireless, and may traverse between the area in which the patient and ventilator are located (e.g. an isolation room) and the external area in which an alternate control system is located (e.g. outside the isolation room). In examples having a wired connection, the wire may be run, for example, from the ventilator controller, through a ceiling of the isolation room to an external alternate control system. Generally, a mechanism may also be provided to ensure that an operator of the alternate control system is within visual range of the patient and/or ventilator. FIG. 3 is a simplified block diagram of a medical ventilation system 30 including a wireless connection according to an embodiment of the present disclosure. Description of components corresponding to components included in FIG. 2 will not be repeated and changes from FIG. 2, including configuration of the communication path will be described. For example, the external interface 4a may include a wireless transmitter and receiver 34a and the internal interface 4b may include a wireless receiver and transmitter 34b. In one embodiment, the wireless receiver and transmitter 34b may be included in the controller 3. The communication path may be implemented using a wireless connection with a transmission range within a predetermined distance to ensure visibility of the ventilator 2 and/or patient 8 by the user in the external area 21a. For example, the wireless transmitter and receiver 34a and the wireless receiver and transmitter 34b may be infrared transmitters/receivers. The medical ventilation system 30 may execute authentication via the wireless connection. For example, the input device 33a may receive identification information, such as a log on identifier and/or password or any other identification information such as biometric information etc. The wireless transmitter and receiver 34a may provide an identification item responsive to the identification information at the input device 33a to the wireless receiver and transmitter 34b. The wireless receiver and transmitter 34b may receive the identification item and may further provide the identification item to the controller 3.

Figure 4:
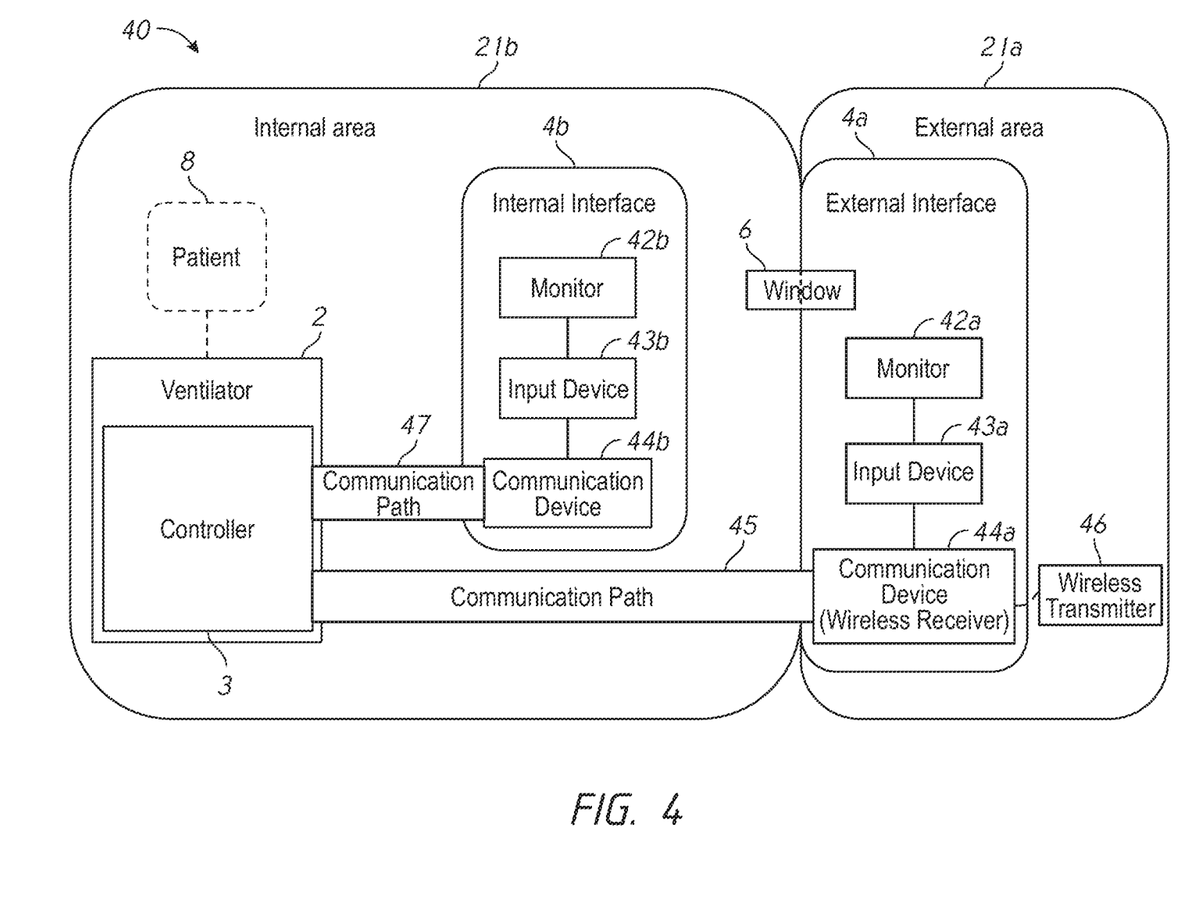
FIG. 4 is a simplified block diagram of a medical ventilation system including wireless authentication according to an embodiment of the present disclosure.

In some examples, an authentication process may be executed wirelessly while a communication path may be provided by wired connection. FIG. 4 is a simplified block diagram of a medical ventilation system 40 including wireless authentication according to an embodiment of the present disclosure. Description of components corresponding to components included in FIG. 2 will not be repeated and changes from FIG. 2, including configuration of the communication path will be described. For example, the communication path 45 may be a wired communication via a cable that may have a length shorter than a predetermined length, to ensure proximity. Alternatively, the communication path 45 may be implemented using wireless communication, such as infrared communication. For example, the external interface 4a may include a communication device 44a that is coupled to a communication device 44a via the communication path 45. In one embodiment, the communication device 44a may include a wireless receiver that may use wireless connection with a wireless transmitter 46 within a predetermined distance from the external interface 4a. The medical ventilation system 40 may execute authentication via the wireless connection between the wireless transmitter 46 and the communication device 44a. For example, contactless authentication may be executed using radio-frequency identification (RFID) or near field communication (NFC). The wireless transmitter 46 may be embedded to a user's belonging, such as a card, a smartphone, etc., uniquely assigned and provided to identify the user. For example, the wireless receiver in the communication device 44a may receive an identification item the contactless authentication via from the wireless transmitter 46. In order to ensure presence of the user, the external interface 4a may include a thermal sensor to detect whether the user, which is an operator of the external interface 4a, is within an area that is proximity of the external interface 4a having visibility of the ventilator 2 and patient 8 from the user. Other sensors may be used in other examples to confirm visibility of the patient and/or ventilator by an operator of the alternate control system. An infrared or other line-of-sight sensor may be placed on the operator and/or the alternate control system, and confirmation of a line-of-sight connection (e.g. receipt of the infrared or other visible indicator at the ventilator or otherwise within the room) may be required before commands from the alternate control system may be provided to the ventilator controller and/or acted on by the ventilator controller. If the user is undetected in the area that is proximity of the external interface 4a having visibility of the ventilator 2 and patient 8 from the user, a command from the user from the external interface 4a may be rejected by the alternate control system and/or the ventilator.

The contactless authentication may be executed in the communication device 44a or in the controller 3. If the contactless authentication is executed at the communication device 44a, the command may be transmitted via the communication path 45 only if authentication has occurred successfully. The communication path 45 may be either wired or wireless. If the authentication is executed at the controller 3, the communication device 44a may provide the identification item to the communication device 44b. The communication device 44b may receive the identification item and may further provide the identification item to the controller 3. The controller 3 may execute the command when the authentication is successful.

Figure 5A:
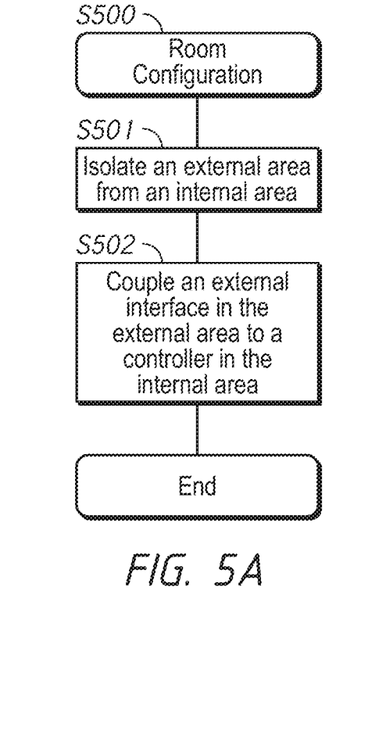
FIG. 5A is a flow diagram of a room configuration of the medical ventilation system, according to an embodiment of the present disclosure.

A medical ventilation system may include a room configuration including an isolation room. FIG. 5A is a flow diagram of a room configuration of the medical ventilation system, according to an embodiment of the present disclosure. Description of the flow diagram of FIG. 5A will be provided with regards to the medical ventilation system 20 of FIG. 2, however, the flow diagram of FIG. 5A may apply to the medical ventilation systems 20, 30, 40 of FIGS. 2 to 4. In the room configuration (S500), an internal area 21b inside an isolation room 1 where a patient 8 is accommodated is clinically isolated (S501) from an external area 21a by a window 6, walls and a door (not shown) or the like. In order to control a ventilator 2 attached to the patient 8 in the isolation room 1 from outside the isolation room 1, an external interface 4a may be provided in the external area 21a. The window 6 may provide a view of the patient 8 and the ventilator 2 from a user while the user is operating the external interface 4a from the external area 21a. The external interface 4a may be electrically coupled to a controller 3 in the internal area 21b that controls the ventilator 2 (S502).

Figure 5B:
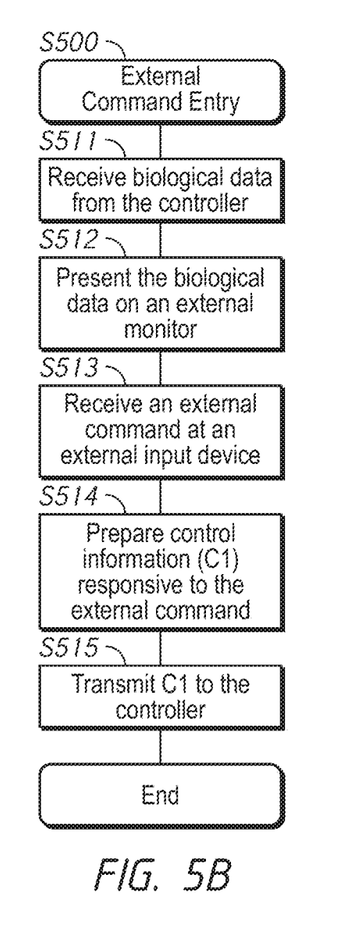
FIG. 5B is a flow diagram of an external command entry of the medical ventilation system, according to an embodiment of the present disclosure.

FIG. 5B is a flow diagram of an external command entry of the medical ventilation system, according to an embodiment of the present disclosure. The flow diagram of FIG. 5B describes processing of an external command (S510) within the external area 21a of the medical ventilation system 20 of FIG. 2, however, the flow diagram of FIG. 5B may apply to the medical ventilation systems 20, 30, 40 of FIGS. 2 to 4. While the medical ventilation system 20 is active, the monitor 22a of the external interface 4a receives biological data (S511), such as patient respiratory frequency, volume, pressure and mechanics, of the patient 8 from the controller 3. The monitor 22a may present the biological data (S512), such as displaying on the monitor 22a, playing voice guidance, etc. and may further prompt the user to enter a command to control an action of the ventilator 2. When the user at the external interface 4a enters an external command from an input device 23a, the input device 23a receives the entered external command (S513). Responsive to the external command, a communication device 24a in the external interface 4a may prepare control information (C1) (S514) and transmit the control information to the controller 3 in the ventilator 2 in the internal area 21b (S515).

Figure 5C:
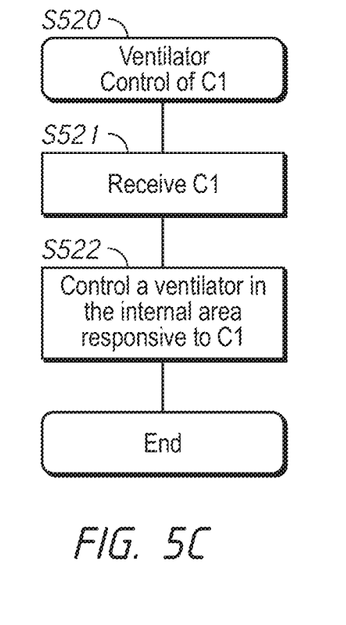
FIG. 5C is a flow diagram of ventilator control of the medical ventilation system, according to an embodiment of the present disclosure.

FIG. 5C is a flow diagram of ventilator control of the medical ventilation system, according to an embodiment of the present disclosure. The flow diagram of FIG. 5C describes ventilator control of the control information in the internal area 21b based on the external command (S520), however, the flow diagram of FIG. 5C may apply to the medical ventilation systems 20, 30, 40 of FIGS. 2 to 4. The controller 3 may receive the control information C1 (S521) from the communication device 24a in the external interface 4a. Based on the control information C1, the controller 3 in the ventilator 2 may control the ventilator 2 (S522) to provide treatment (e.g., providing gas including appropriate concentration of oxygen, etc.) to the patient 8.

Figure 5D:
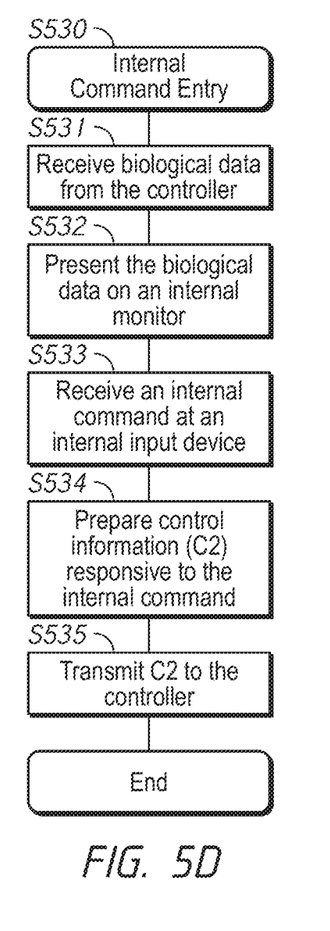
FIG. 5D is a flow diagram of an internal command entry of the medical ventilation system, according to an embodiment of the present disclosure.

FIG. 5D is a flow diagram of an internal command entry of the medical ventilation system, according to an embodiment of the present disclosure. The flow diagram of FIG. 5D describes processing of an internal command (S530) within the internal area 21b of the medical ventilation system 20 of FIG. 2, however, the flow diagram of FIG. 5D may apply to the medical ventilation systems 20, 30, 40 of FIGS. 2 to 4. While the medical ventilation system 20 is active, the monitor 22b of the internal interface 4b receives biological data (S531), such as patient respiratory frequency, volume, pressure and mechanics, of the patient 8 from the controller 3 in the ventilator 2. The monitor 22b may present the biological data (S532), such as displaying on the monitor 22b, playing voice guidance, etc. and may further prompt the user to enter a command to control an action of the ventilator 2. When the user at the internal interface 4b enters an internal command from an input device 23b, the input device 23b receives the entered internal command (S533). Responsive to the internal command, a communication device 24b in the internal interface 4b may prepare control information (C2) (S534) and transmit the control information C2 to the controller 3 (S535). The controller 3 may receive the control information C2 from the communication device 24b. Based on the control information C2, the controller 3 in the ventilator 2 may control the ventilator 2 to provide treatment (e.g., providing gas including appropriate concentration of oxygen, etc.) to the patient 8.

Figure 5E:
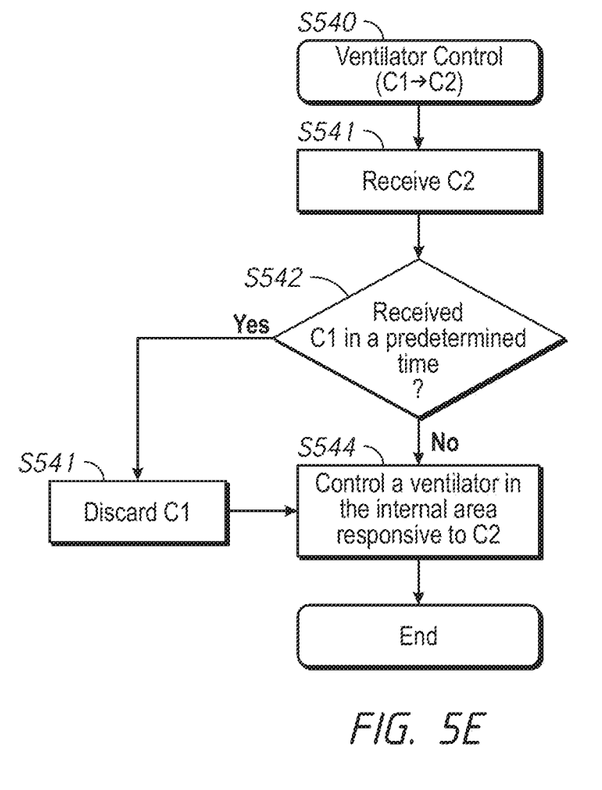
FIG. 5E is a flow diagram of ventilator control of the medical ventilation system, according to an embodiment of the present disclosure.

The controller 3 in the ventilator 2 may control the ventilator 2 responsive to control information C1 based on the external command and control information C2 based on the internal command. FIG. 5E is a flow diagram of ventilator control of the medical ventilation system, according to an embodiment of the present disclosure. Description of the flow diagram of FIG. 5E includes controlling the ventilator 2 when the control information C2 based on the internal command is received just after receiving the C1 based on the external command is received (S540). The flow diagram of FIG. 5E may apply to the medical ventilation systems 20, 30, 40 of FIGS. 2 to 4. The controller 3 may receive the control information C2 from the communication device 24b (S541) after receiving the control information C1 from the communication device 24a. The controller determines whether the control information C1 has been received in a predetermined time from the receipt of the control information C2 (S542). If the control information C1 has been received prior to the predetermined time before the receipt of the control information C2, the controller 3 may continue controlling the ventilator 2 based on the control information C1. If the control information C1 has been received within a predetermined time from the receipt of the control information C2, the controller 3 may discard the control information C1 (S543). In either way, the controller 3 may then control the ventilator 2 based on the control information C2 (S544).

Figure 6:
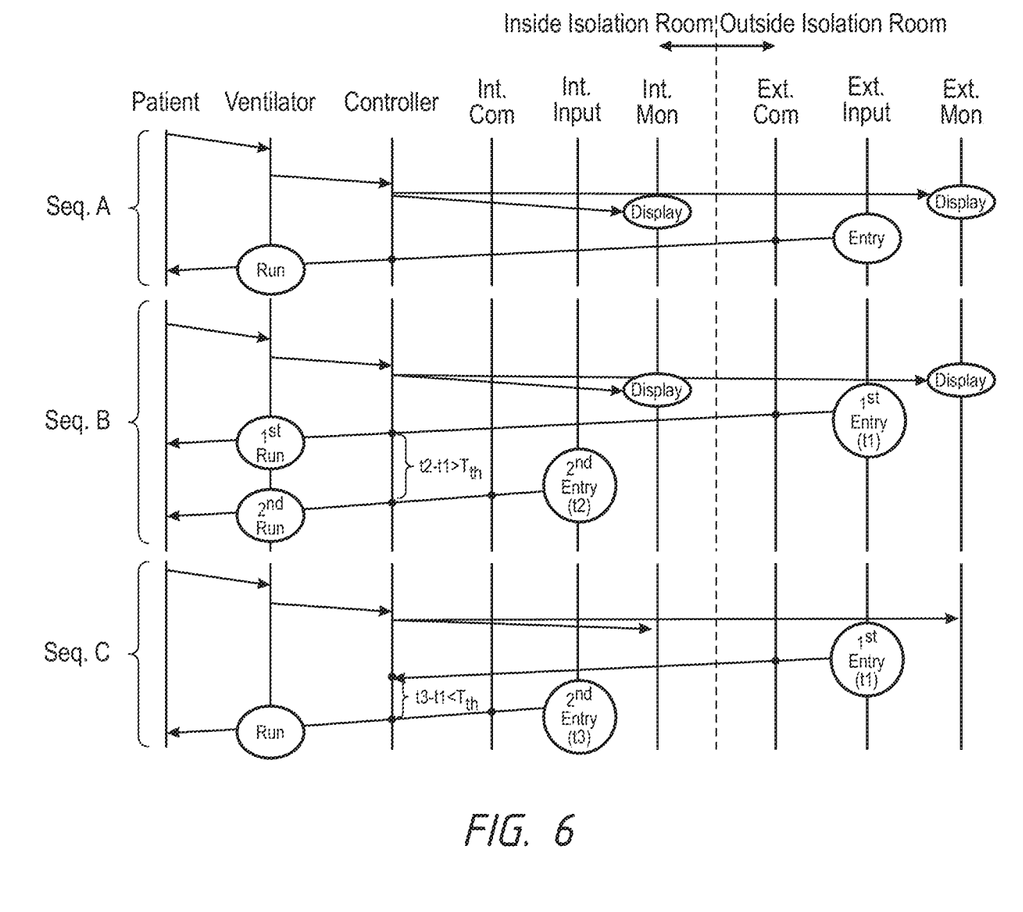
FIG. 6 is a schematic diagram of a communications protocol for the medical ventilation system, according to an embodiment of the present disclosure.

FIG. 6 is a schematic diagram of a communications protocol for the medical ventilation system, according to an embodiment of the present disclosure. Description of the communications protocol of FIG. 6 may refer to components in the medical ventilation system 20 in FIG. 2, although the communications protocol of FIG. 6 may apply to the medical ventilation systems 20, 30, 40 of FIGS. 2 to 4. In a first sequence (Seq. A), the ventilator 2 may collect data from the patient 8 and may further transmit the data to the controller 3 in the ventilator. The controller 3 may transmit the data to the monitor 22a in the external interface 4a and the monitor to 22b in the internal interface 4b. The monitors 22a and 22b may display the data (Display), when the monitors are active (e.g., always, or responsive to a presence of the user in a power save mode, etc.). When the user enters a command (Entry) from the input device 23a in the external interface 4a, the communication device 24a may transmit the command in the external interface 4a to the controller 3. The controller 3 may control the ventilator 2 to execute a ventilation function indicated in the command responsive to the command (Run).

In a second sequence (Seq. B), from the data collection at the ventilator 2 to the data display of at the monitors 22a and 22b may be executed similarly to the first sequence (Seq. A). When the user enters a first command (1$^{st}$ Entry) from the input device 23a in the external interface 4a at t1, the communication device 24a may transmit the command in the external interface 4a to the controller 3. The controller 3 may control the ventilator 2 to execute a ventilation function indicated in the first command responsive to the first command (1$^{st}$ Run). When the user enters a second command (2nd Entry) from the input device 23b in the internal interface 4b at t2, the communication device 24b may transmit the second command in the internal interface 4b to the controller 3. When the difference between t1 and t2 is larger than a threshold time $T_{th}$ (t2−t1>$T_{th}$), the controller 3 may control the ventilator 2 to execute a ventilation function indicated in the second command responsive to the second command (2$^{nd}$ Run) after executing the ventilation function indicated in the first command (1$^{st}$ Run).

In a third sequence (Seq. C), from the data collection at the ventilator 2 to the data display of at the monitors 22a and 22b may be executed similarly to the first sequence (Seq. A). When the user enters a first command (1$^{st}$ Entry) from the input device 23a in the external interface 4a at t1, the communication device 24a may transmit the command in the external interface 4a to the controller 3. When the user enters a second command (2nd Entry) from the input device 23b in the internal interface 4b at t3, the communication device 24b may transmit the second command in the internal interface 4b to the controller 3. When the difference between t1 and t3 is smaller than the threshold time $T_{th}$ (t3−t1<$T_{th}$), the controller 3 may discard the first command and may further control the ventilator 2 to execute a ventilation function indicated in the second command responsive to the second command (Run).

Communication techniques and authentication techniques used in the embodiments described the above are examples. In other embodiments, combinations of communication techniques and authentication techniques other than those specifically described in the present disclosure may be used without departing from the scope of the present disclosure.

Although examples have been disclosed herein, it will be understood by those skilled in the art that the inventions extend beyond the specifically disclosed examples to other alternative embodiments and/or uses and modifications and equivalents thereof. In addition, other modifications which are within the scope of this application will be readily apparent to those of skill in the art based on this disclosure. It is also contemplated that various combinations or subcombinations of the specific features and aspects of the embodiments may be made and still fall within the scope of the application. It should be understood that various features and aspects of the disclosed embodiments can be combined with or substituted for one another in order to form varying examples. Thus, it is intended that the scope of the application should not be limited by the particular examples described herein.

What is claimed is:

1. A medical ventilation system comprising:
   a first interface inside a first area, the first interface comprising:
      a first monitor configured to present data related to control of a ventilator;
      a first input device configured to receive a first command; and
      a first communication device configured to provide the data to the first monitor, and further configured to receive the first command from the first input device and to communicate the first command,
   a second interface inside a second area, the second interface configured to be coupled to the ventilator, the second interface comprising:
      a second monitor configured to present the data;
      a second input device configured receive a second command; and
      a second communication device configured to provide the data to the second monitor, and further configured to receive the second command and to communicate the second command,
   a ventilator inside the second area medically isolated from the first area, the ventilator configured to be visible to the first interface while the first interface is in the first area, and further configured to provide treatment to a patient;
   a controller inside the second area, the controller configured to receive the first command from the first communication device and the second command from the second communication device and further configured control the ventilator responsive to a command received,
   a first communication path coupled to the first communication device and further coupled to the controller, configured traverse between the first area and the second, medically isolated, area and further configured to carry the first command to the controller, and
   a second communication path in the second area, coupled to the second communication device and further coupled to the controller, and further configured to carry the second command to the controller.

2. The system of claim 1, wherein the controller is configured to discard the first command and further configured to control the ventilator responsive to the second command, if the controller receives the second command within a predetermined time from a receipt of the first command.

3. A medical ventilation system comprising:
   a first interface inside a first area, the first interface comprising:
      a first monitor configured to present data related to control of a ventilator;
      a first input device configured to receive a first command; and
      a first communication device configured to provide the data to the first monitor, and further configured to receive the first command from the first input device and to communicate the first command,
   a second interface inside a second area, configured to be coupled to the ventilator, the second interface comprising:
      a second monitor configured to present the data;
      a second input device configured to receive a second command; and
      a second communication device configured to provide the data to the second monitor, and further configured to receive the second command and to communicate the second command, a ventilator inside the second area, the ventilator is configured to be coupled to a body of a patient;

a controller inside the second area, configured to be coupled to the second interface, the controller further configured to receive the first command from the first communication device and the second command from the second communication device and further configured to control the ventilator responsive to a command received, a first communication path coupled the first communication device and further coupled to the controller, the first communication path configured to traverse between the first area and the second area and further configured to carry the first command to the controller, and a second communication path in the second area, coupled to the second communication device and further coupled to the controller, and further configured to carry the second command to the controller, wherein the controller is configured to verify a state that the first interface is visible to the controller responsive to the first command, and further configured to reject the first command if the controller fails to verify the state.

4. The system of claim 3, wherein the controller is configured to verify the state by verifying that the first communication path is a cable having a length shorter than a predetermined length.

5. The system of claim 3, wherein the controller is configured to receive an identification item, and further configured to verify the state based on the identification item.

6. The system of claim 5, wherein the first interface comprises a wireless transmitter and a controller comprises a wireless receiver, wherein the first input device is configured to receive identification information, wherein the wireless transmitter is configured to provide the identification item responsive to the identification information to the wireless receiver, wherein the wireless receiver is configured to receive the identification item and further configured to provide the identification item to the controller, and wherein the controller is configured to verify the state responsive to the identification items from the wireless receiver.

7. The system of claim 3, wherein the first communication path comprises a memory storing the identification item, and wherein the controller is configured to verify the state responsive to the identification item stored in the memory.

8. The system of claim 3, wherein the controller is further configured to provide an alert to a user via the second interface if the controller fails to verify the state.

9. A method of controlling a ventilator, the method comprising:

clinically isolating a first area from a second area;

electrically coupling a first interface in the first area to a controller in the second area;

electrically coupling a second interface in the second area to a controller in the second area;

transmitting first control information to the controller from the first interface of the first area;

transmitting second control information to h controller from the second interface of the second area;

receiving the first control information from the first interface and the second control information from the second interface by the controller in the ventilator in the second area;

verifying a state that the first interface is visible to the controller responsive to receiving the first control information, and accepting the first control information if the state is verified;

and controlling the ventilator in the second area to provide treatment to a patient in the second area by the controller responsive to the accepted first control information.

10. The method of claim 9, further comprising:

providing data related to biological information from the controller in the second area to the first interface in the first area;

presenting the data on a first monitor in the first area;

receiving a first command at a first input device in the first area; and preparing the first control information responsive to the first command to the controller.

11. The method of claim 10, further comprising:

presenting the data on a second monitor in the second area;

receiving a second command at the second interface in the second area; and preparing the second control information responsive to the second command to the controller.

12. The method of claim 11, further comprising:

discarding the first control information responsive to the first command upon a receipt of second control information responsive to the second command within a predetermined time; and controlling the ventilator responsive to the second control information.

13. The method of claim 10, further comprising:

receiving an identification item in the second area; and rejecting the first command if the identification item fails to satisfy a predetermined condition.

14. The method of claim 13, further comprising:

storing the identification item in a memory in a communication path that traverses the first area and the second area, and providing the first control information from the first area to the second area via the communication path.

15. A method of controlling a ventilator, the method comprising:

clinically isolating a first area from a second area;

electrically coupling a first interface in the first area to a controller in the second area;

electrically coupling a second interface in the second area to a controller in the second area;

transmitting first control information to the controller from the first interface of the first area;

transmitting second control information to the controller from the second interface of the second area;

receiving the first control information from the first interface and the second control intimation from the second interface by the controller in the ventilator in the second area;

controlling the ventilator in the second area to provide treatment to a patient in the second area by the controller responsive to the first control information;

providing a view of the ventilator to an operator while the operator is entering the first command in the first area; and restricting a position of the operator within a third area within the first area that the view is available to the operator.

16. The method of claim 15, further comprising providing the first control information from the first area to the second area via a communication path,
wherein the communication path is a cable having a length shorter than a predetermined length.

17. The method of claim 15, further comprising providing the first control information from the first area to the second area via a communication path,
wherein the communication path is wireless connection with a transmission range within a predetermined distance.

18. The method of claim 15, further comprising:
detecting whether the operator is within the third area; and
rejecting the first command if the operator is undetected within the third area.

* * * * *